(12) United States Patent
Zolli

(10) Patent No.: US 9,101,362 B1
(45) Date of Patent: Aug. 11, 2015

(54) FASTENERS THAT BRING INTO APPOSITION SIDES OF WOUND

(76) Inventor: Christine L. Zolli, Oldwick, NJ (US)

( * ) Notice: Subject to any disclaimer, the term of this patent is extended or adjusted under 35 U.S.C. 154(b) by 1656 days.

(21) Appl. No.: 12/347,375

(22) Filed: Dec. 31, 2008

(51) Int. Cl.
*A61B 17/08* (2006.01)
*A61B 17/122* (2006.01)

(52) U.S. Cl.
CPC .................................. *A61B 17/122* (2013.01)

(58) Field of Classification Search
CPC ............. A61B 17/122; A61B 17/1285; A61B 17/083; A61B 17/10; A61B 17/1227; A61B 17/08
USPC .................................. 606/213, 215, 216, 221
See application file for complete search history.

(56) References Cited

U.S. PATENT DOCUMENTS

| | | | |
|---|---|---|---|
| 2,966,907 A * | 1/1961 | Fasolino | 606/74 |
| 4,535,772 A | 8/1985 | Sheehan | |
| 5,171,252 A * | 12/1992 | Friedland | 606/151 |
| 5,618,311 A | 4/1997 | Gryskiewicz | |
| D381,119 S | 7/1997 | Chang | |
| D410,302 S | 5/1999 | Yasuda | |
| 6,165,204 A | 12/2000 | Levinson | |
| 7,267,682 B1 | 9/2007 | Bender | |
| 2005/0182426 A1 * | 8/2005 | Adams et al. | 606/142 |
| 2006/0195125 A1 | 8/2006 | Sakakine | |
| 2010/0030245 A1 * | 2/2010 | Kassab et al. | 606/157 |

* cited by examiner

*Primary Examiner* — Gregory Anderson
(74) *Attorney, Agent, or Firm* — Hess Patent Law Firm LLC; Robert J. Hess

(57) ABSTRACT

A surgical fastener that has an urging part and a piercing part. The urging part is formed to urge the piercing part to move between open and closed positions. The piercing part includes a pair of piercing prongs that terminate at tips, which taper into a sharpened condition to pierce through skin tissue under manual force. The piercing prongs each having a different radius of curvature so that the tips overlap each other as the piercing part reaches the closed position and that spread apart from each other as the piercing part reaches the open position. At least one of the urging part and the piercing part including a mechanism that tends to urge the tips of the piercing prongs closer to each other as the piercing part moves to the closed position from the open position.

9 Claims, 8 Drawing Sheets

_US 9,101,362 B1_

FASTENERS THAT BRING INTO APPOSITION SIDES OF WOUND

BACKGROUND OF THE INVENTION

1. Field of the Invention

The present invention relates to external skin wound fasteners that are employed for rapid closure of skin wounds by bringing sides of the wound into apposition. Apposition is a layered formation of superficial and deep soft tissues beginning at the skin surface. Hard tissue as cartilage, bone, enamel, dentin, and cementum may lie beneath the apposition and thus can benefit by being stabilized by fasteners securing the tissue above. The fasteners may be clips, clasps or uniters.

2. Description of Related Art

Skin wounds may be closed with surgical fasteners (clips and skin staples), sutures, Ethicon dermabond, or Gecko-inspired surgical tape.

Skin wounds of shallow depths (3.9 mm) are closed by skin staples, but cannot close deep wounds. Deep wounds are closed now with sutures in layers and only the surface is stapled with staples.

Ethicon dermabond is a skin bond glue—liquid that hardens in contact useful only for small tension free cuts (such as for children who are afraid of needles). Gecko-inspired surgical tape is made of a biodegradable elastic polymer and is suitable to patch wounds in organs such as the liver or heart.

Surgical fasteners (including clips and staples) and mentioned in U.S. Pat. No. 5,618,311 permit the surgeon to rapidly close a wound with a mechanical fastener, which holds the tissue together while the wound heals. These present day surgical fasteners however reach only to shallow depths and cannot appose bulky tissue masses. Both metallic and non-metallic fasteners are in common use. Some of the non-metallic fasteners are formed from bio-absorbable resinous materials such as blends of lactic acid/glycolide copolymer. Plastic materials of this type are widely known and commercially available under the trade names of "POLYSORB" and "LACTOMER" plastic. Typically fasteners made from these materials lose a substantial portion of their tensile strength after a few weeks of exposure to human tissue. After deployment in a mammalian body, the fasteners fragment and the pieces are metabolized by the body and therefore dissolve over time.

According to U.S. Pat. No. 5,618,311, the principal advantage of surgical stapling is the speed with which a wound or incision can be closed. However, in certain surgical procedures it is desirable to close the skin wound with sutures lying completely in the dermis layer. This form of subcuticular suturing minimizes the occurrence of visible scarring. However, such subcuticular suturing is very tedious and is very time consuming to perform. Surgical staplers and clips are not available for performing this type of closure.

U.S. Pat. No. 5,618,311 proposed a biodegradable surgical fastener having noninterlockable members. The fastener comprises a first arm and a second arm integrally interconnected to each other. Each arm has a distal prong such that each of the distal prongs are directed toward the other arm. Also proposed is a surgical fastener applicator for applying surgical fasteners having arms each with a prong. This staple-gun like applicator extrudes the biodegradable fastener horizontally to stay parallel to the skin surface in the dermis of the skin, and it is thus not meant to appose in vertically made deep tissue wounds.

Such an applicator comprises a fixed handle, a movable applicator lever mounted for motion with respect to said fixed handle, an applicator nose mounted to the fixed handle for storing a plurality of the fasteners and for positioning a fastener at the distal end of the applicator nose, spreader pins located proximate the applicator nose and contacting the fastener, and means connected to the spreader pins and the applicator lever for translating the movement of the applicator lever to the spreader pins. As the applicator lever is actuated, for example, when it is moved into the fixed handle, the spreader pins first apply pressure on the arms to spread apart the prongs of the fastener and subsequently release the pressure on the arms to allow the prongs to approach each other. The applicator can further have squeezer jaws located proximate the applicator nose and coupled to the movable applicator lever so that motion is translated from the applicator lever to the squeezer jaws when the applicator lever is actuated, for example, when the lever is moved into the handle. The squeezer jaws first open to allow the prongs to be spread apart by the spreader pins and subsequently close to apply pressure on the arms to bring the prongs of said fastener together after the spreader pins release the pressure on the arms to allow the prongs to approach each other.

It is desired to provide a surgical fastener suited for closing, at a rapid rate, deep wounds. It is further desired that such a surgical fastener be quickly removed when desired to do so. It is desired to not only close in the dermis, but for deeper wounds, to close fascia and muscle layers all at once if need be.

SUMMARY OF THE INVENTION

One aspect of the present invention relates to external skin wound fasteners that are employed for rapid closure of skin wounds by bringing sides of the wound into apposition. Skin and deeper layers, such as fascia and muscle layers, can be apposed with larger sized fasteners all in one action in accordance with the invention. The fasteners may be clips, clasps or uniters.

Another aspect of the invention resides in a surgical fastener that has an urging part and a piercing part. The urging part is formed to urge the piercing part to move between open and closed positions. The piercing part includes a pair of piercing prongs that terminate at tips, which taper into a sharpened condition to pierce through skin tissue under manual force. The piercing prongs each having a different radius of curvature so that the tips overlap each other as the piercing part reaches the closed position and that spread apart from each other as the piercing part reaches the open position. At least one of the urging part and the piercing part including a mechanism that tends to urge the tips of the piercing prongs closer to each other as the piercing part moves to the closed position from the open position.

The tips of the piercing prongs may be magnetically attracted to each other. The piercing prongs may expand in response to exposure to skin temperature.

A further aspect of the invention resides in a surgical fastener suited for closing, at a rapid rate, deep wounds in the dermis layer and those deeper than the dermis layer and be quickly removed when desired to do so.

BRIEF DESCRIPTION OF THE DRAWING

For a better understanding of the present invention, reference is made to the following description and accompanying drawing, while the scope of the invention is set forth in the appended claims.

DETAILED DESCRIPTION OF THE INVENTION

Unlike suturing, which requires a surgical tray and skilled medical personnel in operating room or emergency room setting, the present invention offers an alternative based on the use of sterile packaged fasteners in various sizes instead. The various sizes are suited for various depths of wounds. Such renders them available to surgeons of many specialties in the operating rooms, emergency rooms and nursing outposts in emergency medical service ambulances. Soldiers may carry them in their backpacks on the battlefield to clasp closed their bleeding wounds immediately when laceration occurs, thereby stopping the loss of blood right away.

Figure 1:
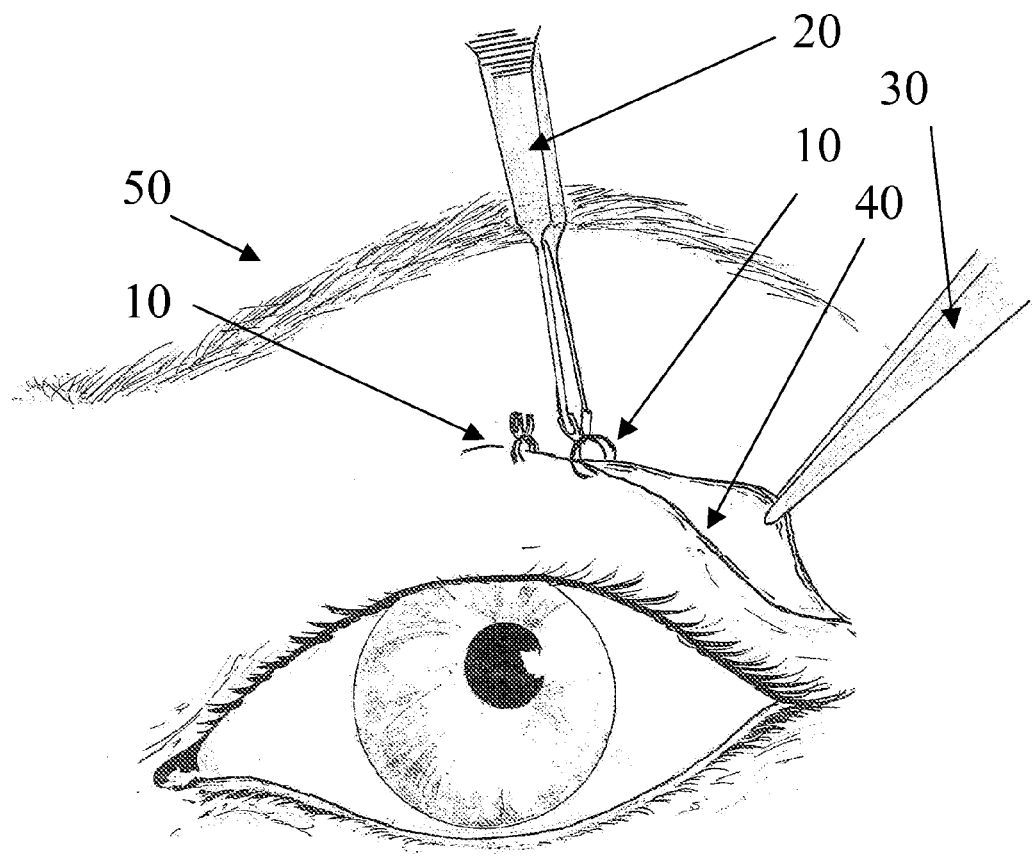
FIG. 1 shows a schematic diagram of a would neighboring the eye in a taut condition due to a grasping force from a surgical tool as the wound is being closed with surgical fasteners in accordance with the invention. Forceps position the surgical fastener appropriately with distal ends of the forceps fitted into accommodating grooves at ends of handles of a surgical fastener.
Figure 2:
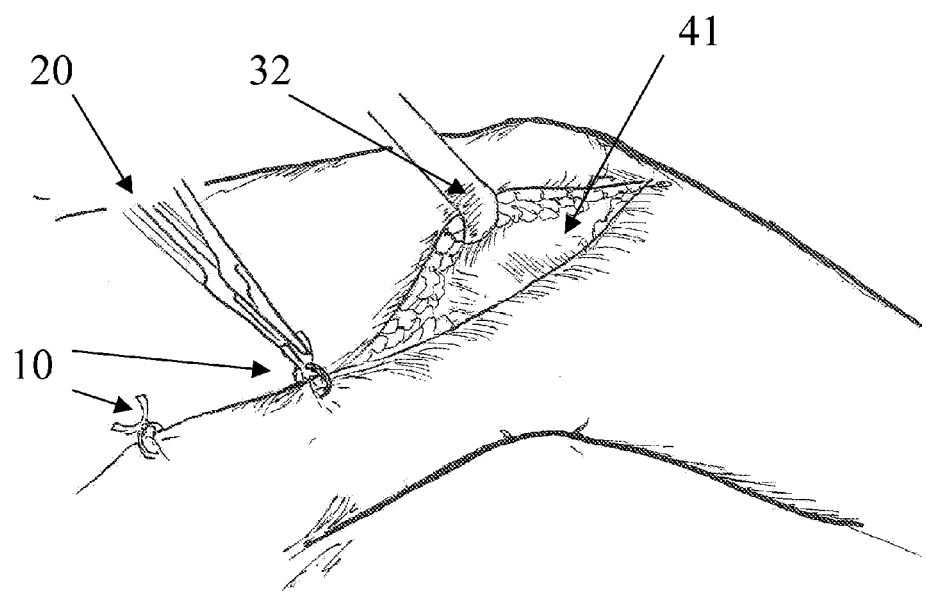
FIG. 2 shows a schematic diagram of the surgical fastener of FIG. 1 but close-up and with a different surgical tool grasping s wall of the wound to render the wound taut as the wound is being closed with surgical fasteners in accordance with the invention. Large wounds can be held taut and made to stay approximated with fingers alone holding the two edges together to "feed" the wound line to the fastener.

Turning to FIG. 1 the surgical fastener 10 is held by forceps 20, while a surgical hook 30 holds open a wound 40 to be closed by a series of the surgical fasteners 10 in the vicinity of an eye 50. FIG. 2 shows a similar view as in FIG. 1, except that a surgical hook 32 is used to open a large wound 41.

Figure 3:
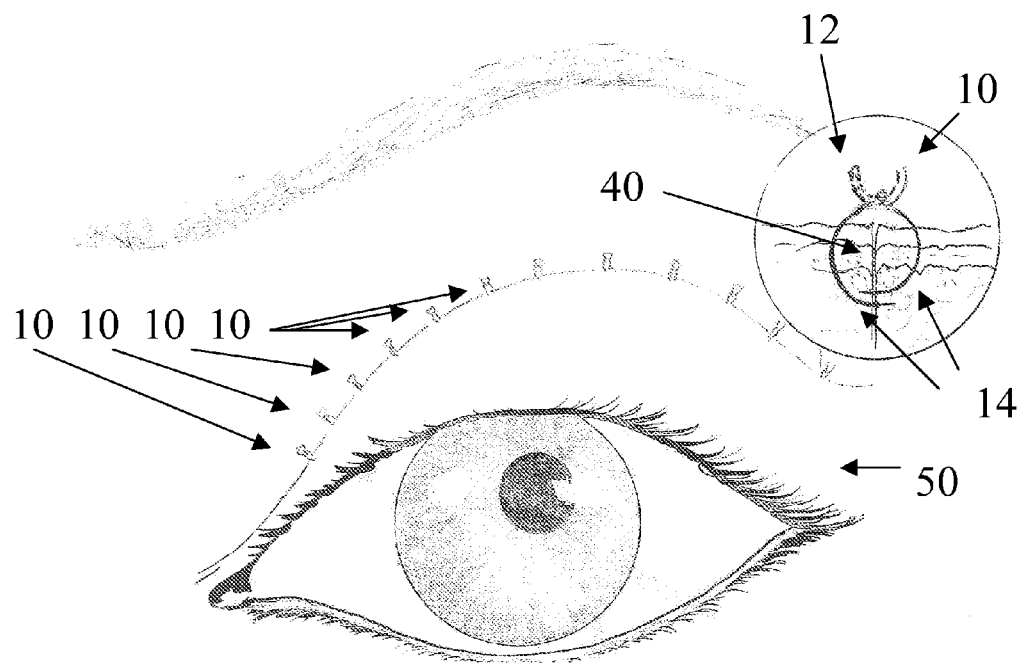
FIG. 3 shows a schematic view of a plurality of surgical fasteners in position closing a wound neighboring the eye, with an inset cut-away view showing an exemplary one of the surgical fasteners in a cut-away view closing the wound.

The purpose for using the surgical fastener 10 is so that lips of he wound would be brought to stay apposed with one pinching motion. The action would close the skin wound quickly as these surgical fasteners 10 would be placed one after another in quick succession at intervals so as to have the closure along the full length of the wound in no time (See FIG. 3).

Figure 4:
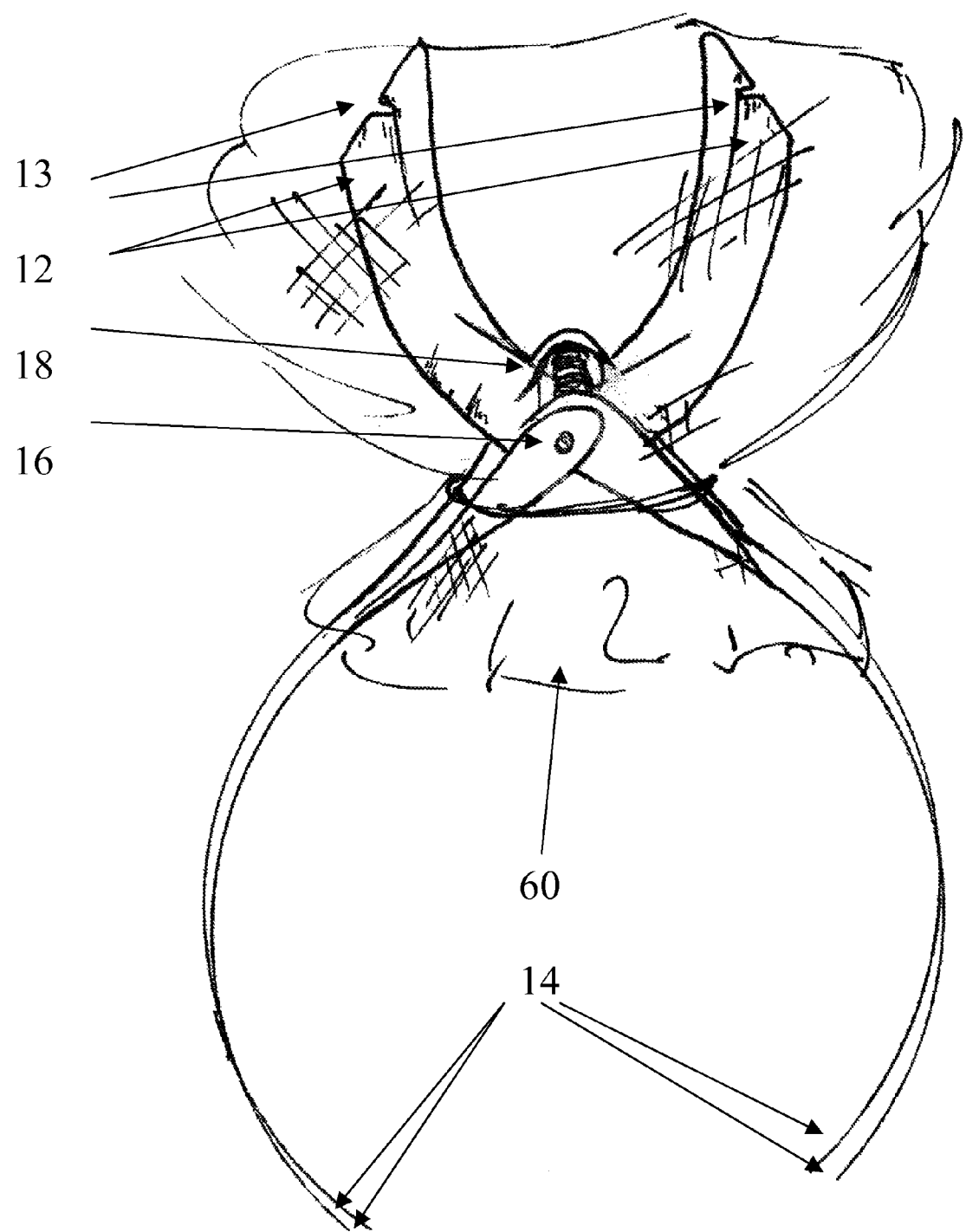
FIG. 4 shows a small-size surgical fastener in accordance with the invention, but with a sterile package enclosing the handles and with grooves in the handle ends for accommodating placement of distal ends of forceps in the manner of FIG. 1.
Figures 5, 6:
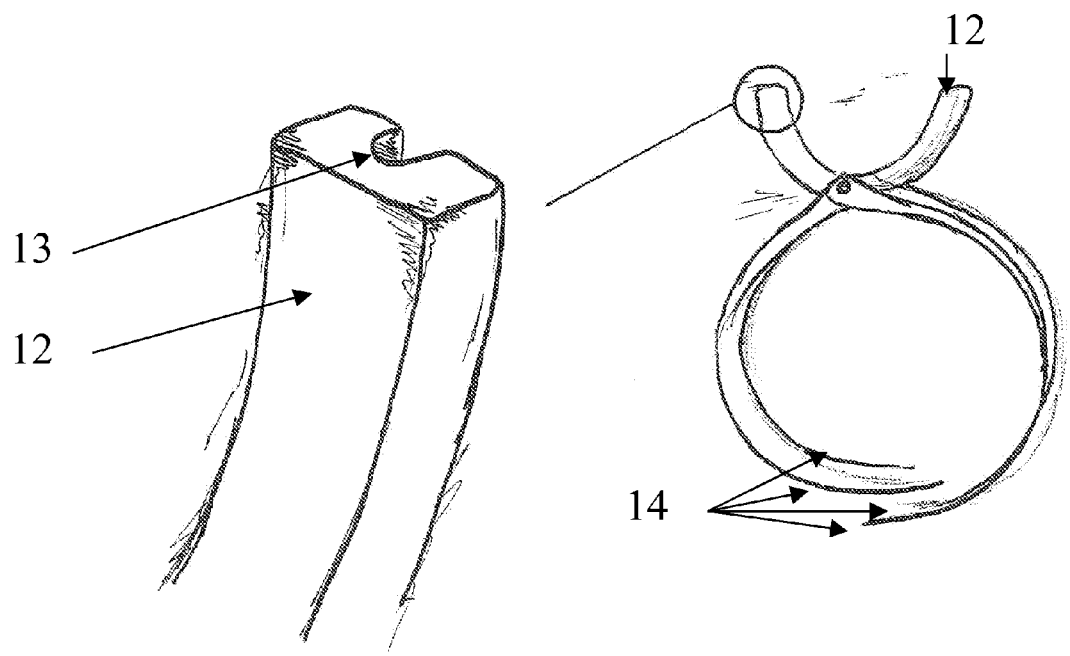
FIG. 5 shows an isometric view of the small-size surgical fastener of FIG. 4 outside the packaging.
FIG. 6 shows an enlargement of a distal end of a handle within the circled portion of FIG. 5 to show the groove to accommodate a distal end of forceps.

Turing to FIGS. 4-6, the surgical fastener 10 is a clasp having external handles 12 (external urging part) each with a groove 13 and a pair of piercing prongs 14 (internal penetrating part or piercing part), a pivot bar 16, and a torsion spring 18. By engaging distal ends of the forceps 20 of FIGS. 1 and 2 into complementary ones of the groves 13 (FIGS. 4 and 6) at the end of the handles 12 and squeezing the forceps 20 (FIGS. 1 and 2) to close, the torsion spring 18 (FIGS. 4 and 5) compresses to open the clasp and thus spread apart the piercing prongs 14. The distal tips of the piercing prongs 14 may be properly positioned relative to the opposite edges of the wound 40 (FIGS. 1 and 2) so that opening the forceps decompresses the spring to enable the piercing prongs 14 to be urged to pierce (penetrate or otherwise enter) from the opposite sides of the wound through the skin. These piercing prongs 14 overlap in deeper parts of the wound apposing the wound sides one to he other as the spring compression would be let go.

The fasteners may come in various sizes. That is, tiny for shallow wounds as those found on the skin of the eyelids to grades of ever larger ones for very deep gushing wounds. For deep wounds, it wound be possible to make two-tier vertically aligned prongs. The tips of the piercing prongs 14 are needle sharp for passing into tissues with ease and thus taper to their distal ends. The piercing prongs 14 may be made of stainless steel or other metals or other tissue compatible materials such as silicone rigid plastic.

Figure 7:
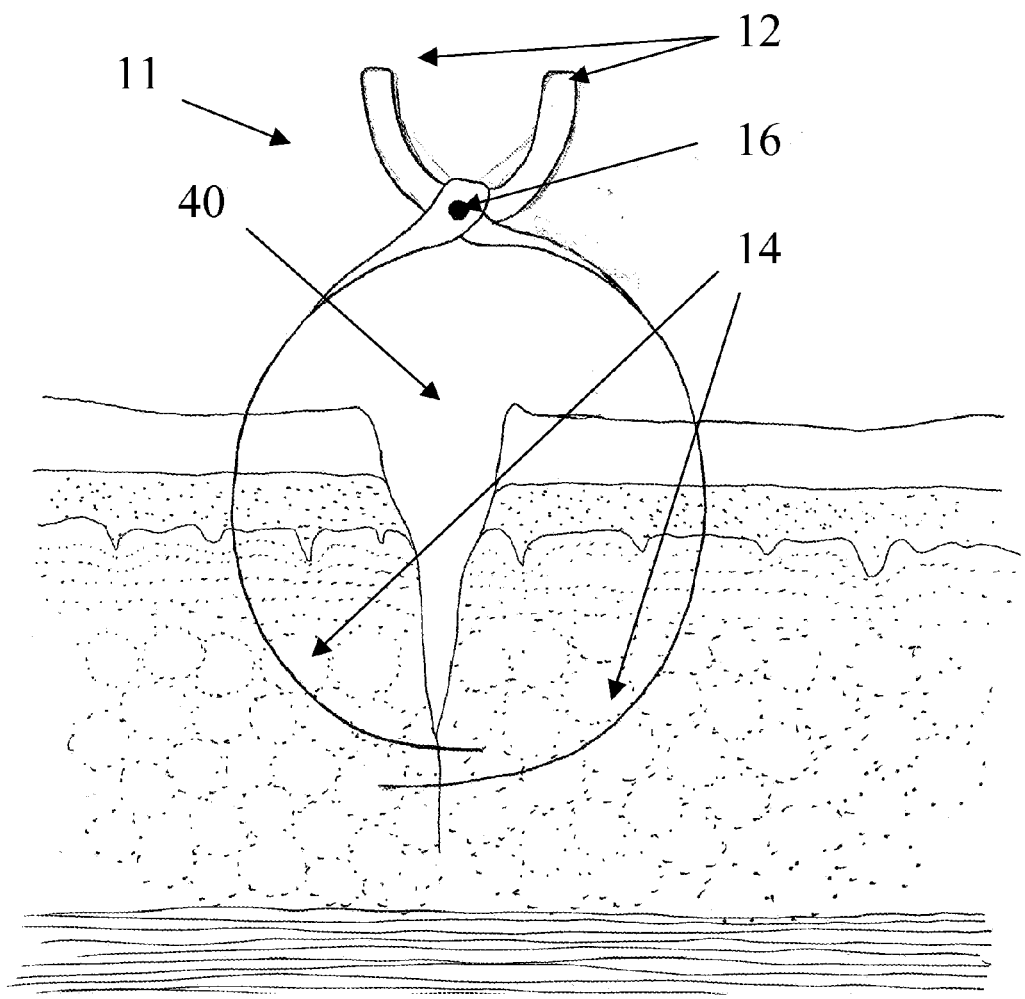
FIG. 7 shows a large-size surgical fastener in accordance with the invention being position to close a wound.
Figure 8:
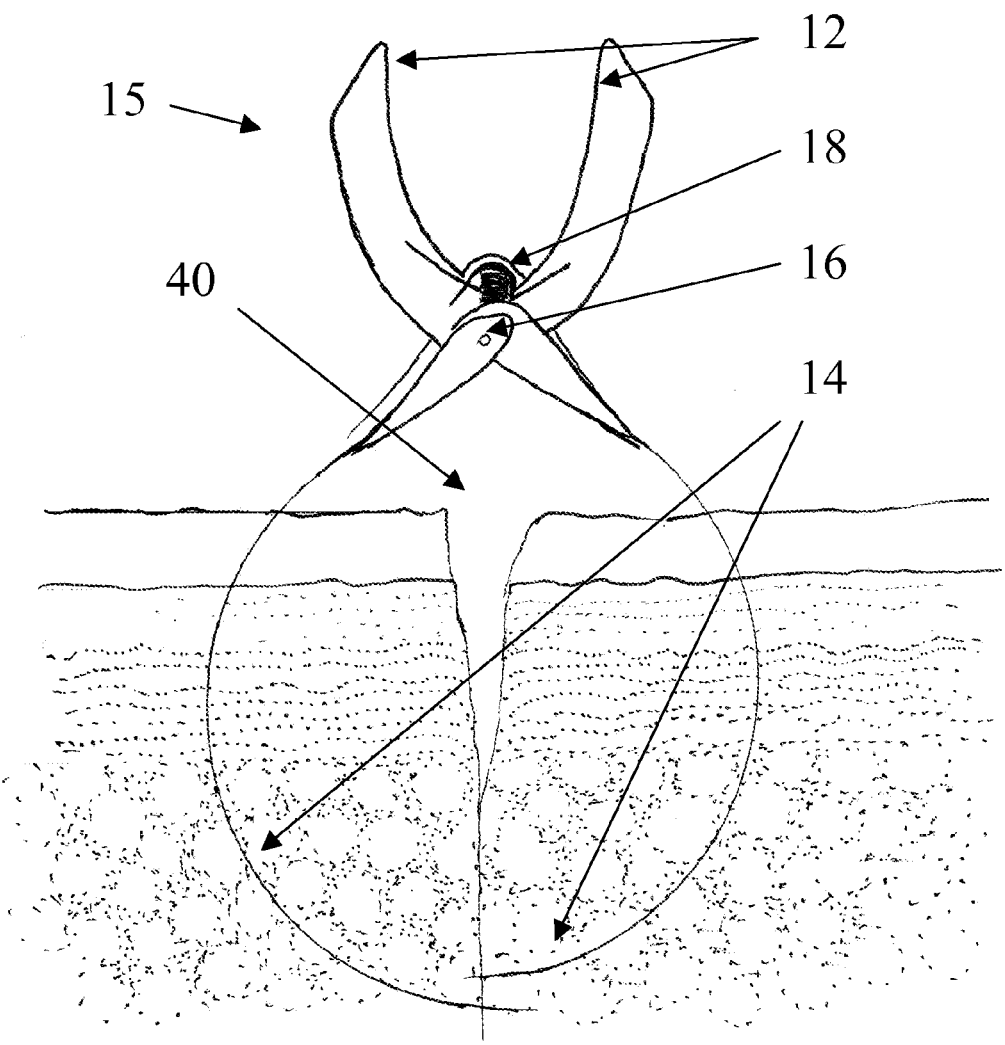
FIG. 8 shows the similar view to that of FIG. 7, except that a torsion spring is provided.

Turning to FIGS. 7 and 8, larger size surgical fasteners 11, 15 are picked up and held by fingers to urge the piercing prongs 14 to penetrate the skin to close the wound 40. In the case of FIG. 8, the torsion spring 18 is compressed by squeezing together the handles 12. The wounds sides are held in apposition by the force of the torsion spring 18 and by the sharpness of tips of the piercing prongs 14.

The surgical fasteners 10, 11 are in a variety of different widths. The dimensions for the different widths are dependent upon the number of prongs of the surgical fastener: 1 prong, 2 prongs, 3 prongs, 4 prongs, n prongs.

Removal of the surgical fasteners 10, 11 is easy. Just pinch a "collar" (squeeze together handles 12) to compress the spring, which causes the piercing prongs 14 to open up and retract out of the healed wound.

The spring 18 does not have to be the sole force or mechanism to keep sides of the wound together and may be dispensed with altogether (FIG. 7). The distal end of the clasps may be magnetic so that a magnetic attractive force would help keep the sides of the wound together. The clasp itself may exert a force tending to keep its prongs in a closed position upon the attainment of certain modalities such as temperature. For instance, the piercing prongs 14 may be made of a metal material that expands when exposed to the elevated temperature of a persons skin temperature at the wound from an unexpanded state at room temperature to generate a force tending to keep sides of the wound together.

Figure 9:
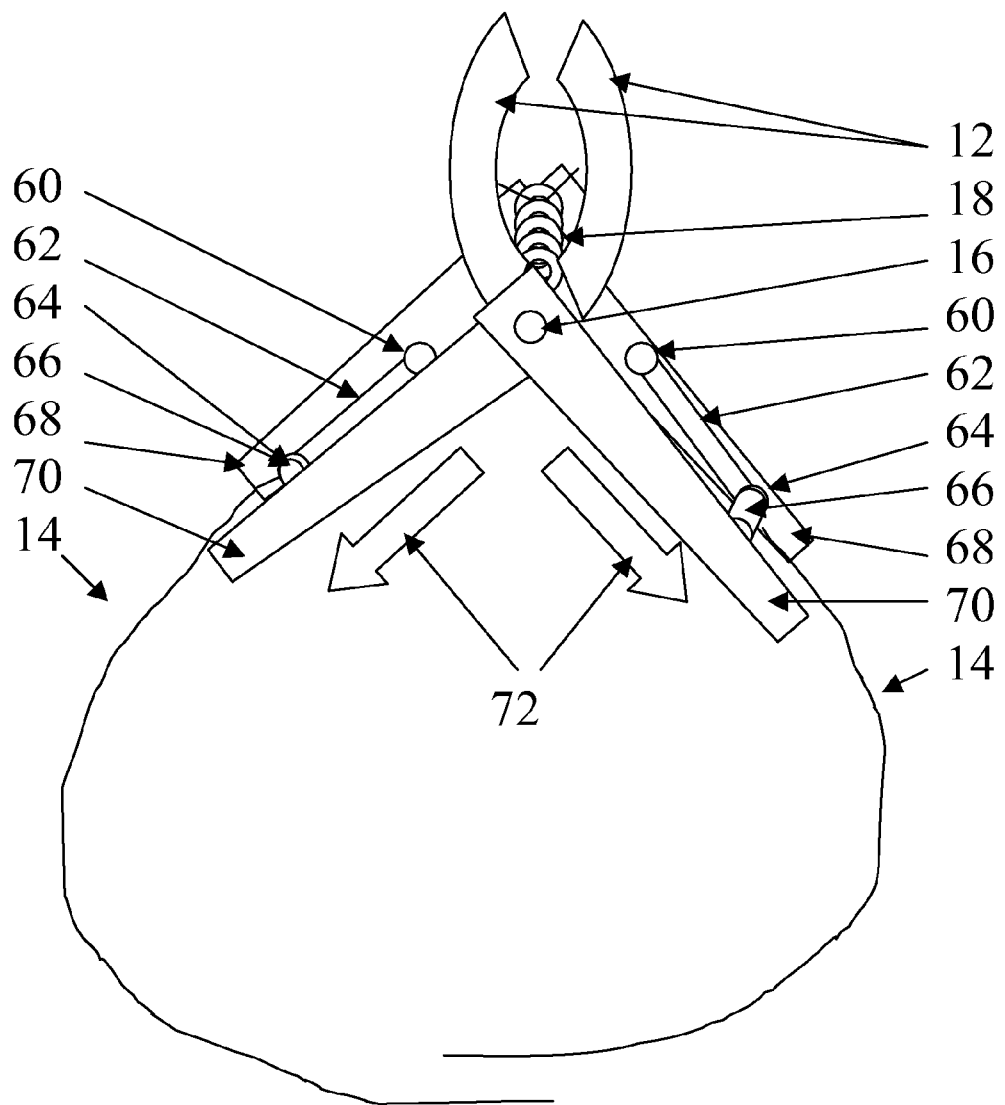
FIG. 9 shows a schematic elevation view of a further embodiment of a fastener with telescoping piercing arms that project from left and right side fastener arms.

Another variant is shown in FIG. 9. The two piercing prongs 14 each telescope in a sense from an associated one of the two fastener legs to overlap each other in the fully extended position of FIG. 9. Each of the piercing prongs spring bias to be urged, upon release, from a retracted position to the fully extended position.

In the retraced position, spring biased pins 66 project through a proximal opening 60 in one outward wall 68 of associated fastener legs. This spring biased pins 66 may taper into the proximate opening 60 such that only the tip can project through. The wider part of the taper is too wide to fit into the proximal opening 60. At the end of the pin opposite from the taper of the pin 66 is a respective spring, which acts against a companion outward wall 70 (spaced from the outward wall 68). Each fastener leg has its own pair of outward walls 68, 70 that are essentially parallel with each other.

Figure 10:
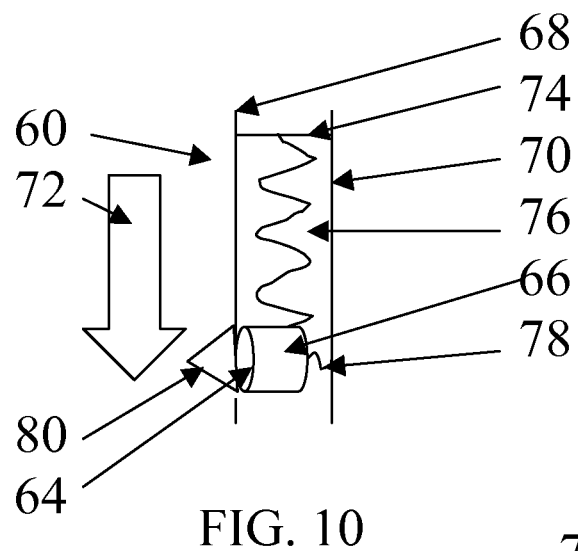
FIG. 10 shows a schematic top view of a left side fastener arm of FIG. 9.
Figure 11:
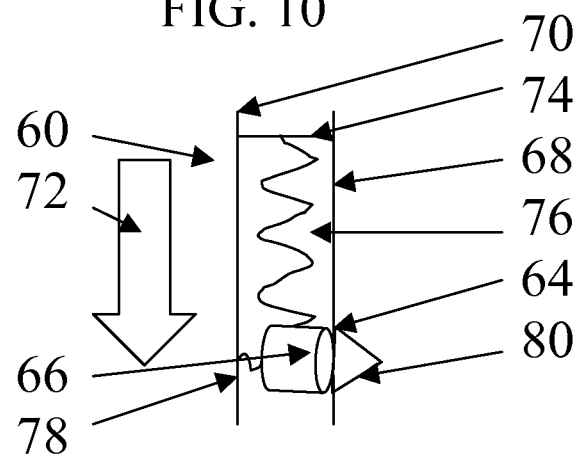
FIG. 11 shows a schematic top view of a right side fastener arm of FIG. 9.

In order for the piercing prongs to move from the retracted position to the fully extended position, catches (pins 66) are released to allow springs 76 to decompress to urge the piercing prongs 14 (FIG. 9) to move in the direction of arrows 72 (FIGS. 9-11). To release the catches, projecting tapered ends 80 (FIGS. 10, 11) of the pins 66 are manually pressed into the proximal openings 60 to clear them. This allows an associated compressed spring 76 (FIGS. 10, 11), which is secured to an associated support bar 74 (FIGS. 10, 11), to decompress to urge the piercing prongs 14 (FIG. 9) to move to the fully extended position while the pins 66 are being guided along tracks 62. The tracks 62 are aligned with each other in both outward walls 68, 70 of associated fastener legs.

At the fully extended position, the tapered ends 80 (FIGS. 10, 11) of the pins 66 bias into associated distal openings 64 just as they did for the proximal openings 60. This effectively locks the piercing prong into its fully extended position. Thus, the piercing prongs 14 travel in the direction of the double arrows 72 (FIGS. 9-11) to reach the fully extended position from the retracted position.

The spring bias of springs 76 that urge the piercing prongs 14 to move from the retracted to the fully extended position is advantageous by providing in effect a stronger push in close proximity to where the piercing prongs are to overlap each other in the fully extended position. Thus, one would initially push the piercing prongs as far as practical into the skin walls on either side of the wound while the piercing prongs are in the retracted position. For instance, as the distal ends of the fastener arms become adjacent the skin, the piercing prongs 14 cannot be further inserted under manual force. At that point of advance, the pins 66 need to be manually pushed in to allow a spring to decompress to urge the piercing prongs to advance further reach their fully extended positions. The sides of the wound should appose each other.

FIG. 10 represents schematically the left side fastener arm of FIG. 9. The left side fastener arm of FIG. 10 is symmetric to the right side fastener arm of FIG. 11. The tracks 62 (FIG. 9) are recesses in the walls 68, 70 of FIGS. 10, 11 that extend the same length, although not shown in those views.

The springs 76 of FIGS. 10, 11 are shown in a decompressed condition, but their compressed condition can be understood when the pins 66 align with the opening 60 such that the tapered ends 80 project through. The springs 76 compress between their associated support bar 74 and the associated pin 66.

The walls 68, 70 may be joined to each other at each fastener leg by top and bottom surfaces (not shown, but which may extend the full distance of the walls 68, 70 to form a rectangular, tubular shape with the walls 68, 70). Movement of the piercing prongs from the retracted position to the extended position appears to telescope from the associated fastener leg.

Removal of the fastener is straightforward. By squeezing the handles 12 toward each other, the fastener legs spread apart, which enables the piercing prongs 14 to be thereafter manually pulled out by pulling out the fastener.

Spring loaded prongs: initially, the prongs would be partially retracted into a sleeve housing a compressed spring. The upper part of the prong would be attached to the spring. A button would be triggered or a pin would be pushed out to release the spring and, as the spring expanded, it would drive the prongs forcefully into fascia.

While the foregoing description and drawings represent the preferred embodiments of the present invention, various changes and modifications may be made without departing from the scope of the present invention.

What is claimed is:

1. A surgical fastener comprising: surgical fastener means for bringing sides of an external skin wound into apposition and for retracting out of the external skin wound after the external skin wound heals, said surgical fastener means including a clasp having an urging part and a piercing part, the urging part being formed to urge the piercing part to move between open and closed positions, the piercing part including a pair of piercing prongs that terminate at tips, the tips tapering into a sharpened condition to pierce through skin tissue under manual force, one of the piercing prongs and an associated one of the tips being configured to define a common radius of curvature along an entirety of their respective lengths, another of the piercing prongs and associated another one of the tips each being configured to define a further radius of curvature that differs from the common radius of curvature along an entirety of their respective lengths so that the tips overlap each other as the piercing part reaches the closed position and that spread apart from each other as the piercing part reaches the open position, at least one of the urging part and the piercing part including a mechanism that tends to urge the tips of the piercing prongs closer to each other as the piercing part moves to the closed position from the open position, the clasp including a pivot that pivotally connects the piercing prongs to each other to allow the piercing prongs to pivot between the open and closed positions, the mechanism including a torsion spring arranged to exert a bias that urges the piercing prongs to pivot about the pivot in one direction into the closed position, the urging part including a pair of handles arranged so that squeezing the pair of handles toward each other under manual force causes the piercing prongs to pivot about the pivot in a reverse direction into the open position against the bias of the torsion spring.

2. The surgical fastener of claim 1, wherein the clasp includes a plurality of sets of the pairs of piercing prongs, the pivot including a pivot bar, the pivot bar and the torsion spring being elongated to extend between the sets of the pairs of piercing prongs.

3. The surgical fastener of claim 1, wherein the mechanism includes distal ends of the piercing prongs being magnetically attracted to each other.

4. The surgical fastener of claim 1, wherein the piercing prongs are elongated, the mechanism including distal ends of the piercing prongs expanding in response to exposure to skin temperature adjacent a wound in a direction of elongation of the piercing prongs.

5. The surgical fastener of claim 1, wherein the piercing prongs are each composed of stainless steel.

6. The surgical fastener of claim 1, wherein the piercing prongs are composed of a material that renders them magnetically attracted to each other.

7. The surgical fastener of claim 1, wherein the piercing prongs are composed of a tissue compatible material.

8. The surgical fastener of claim 1, wherein the urging part includes a pair of fastener legs, the mechanism includes a catch and springs, the springs being arranged to exert a spring bias on the piercing prongs to move the piercing prongs from retracted positions to extended positions with respect to an associated one of the fastener legs upon release of the catch.

9. The surgical fastener of claim 8, wherein the piercing prongs telescope with respect to associated ones of the fastener legs to move from the retracted positions to the extended positions.

* * * * *